United States Patent [19]

Evans et al.

[11] 4,020,100
[45] Apr. 26, 1977

[54] HYDROXAMIC BETAINES

[75] Inventors: William Price Evans, Wirral; Appayya Raghunath Naik, Birkenhead, both of England

[73] Assignee: Lever Brothers Company, New York, N.Y.

[22] Filed: Dec. 3, 1975

[21] Appl. No.: 637,249

Related U.S. Application Data

[63] Continuation of Ser. No. 396,933, Sept. 13, 1973, abandoned.

[30] Foreign Application Priority Data

Sept. 19, 1972 United Kingdom .......... 43274/72

[52] U.S. Cl. .................. 260/501.13; 252/8.8; 252/528; 252/547; 252/DIG. 13; 260/293.76; 260/500.5 H; 260/567.6
[51] Int. Cl.$^2$ .............. C07C 103/70; C07C 101/04
[58] Field of Search ................ 260/500.5 H, 501.13

[56] References Cited

UNITED STATES PATENTS

| | | |
|---|---|---|
| 2,774,786 | 12/1956 | Erickson .................. 260/502.5 |
| 3,113,026 | 12/1963 | Sprung ..................... 260/501.13 |
| 3,738,937 | 6/1973 | Kautsky ................... 260/501.12 |

OTHER PUBLICATIONS

Lange, "Handbook of Chemistry", 1961, pp. 1201, 1202.

*Primary Examiner*—Joseph E. Evans
*Attorney, Agent, or Firm*—Kenneth F. Dusyn; James J. Farrell; Melvin H. Kurtz

[57] ABSTRACT

A new class of compounds having fabric softening properties is formed by hydroxamic betaines having the general formula $R^1(R^2)(R^3)N^+ - R^4 - CO - NH - O^-$ in which $R^1$, $R^2$, $R^3$, $R^4$ are hydrocarbon groups having 1-25 carbon atoms with the proviso that the betaine contains not more than 45 carbon atoms, at least one carbon chain of at least 12 carbon atoms and the carbon chain of $R^4$ between the quaternary N-atom and the CO— group is no longer than 4 carbon atoms. The compounds, which can be used in a fabric softening rinse composition as well as in a detergent composition, remain in dispersion during the washing process, but deposit onto the fabric when the pH decreases during subsequent rinsing.

5 Claims, No Drawings

HYDROXAMIC BETAINES

This is a continuation of application Ser. No. 396,933, filed Sept. 13, 1973, now abandoned.

This invention relates to a new class of compounds for use in detergent compositions, to methods of preparing the compounds, to compositions containing the compounds and to washing processes and fibre treating processes involving their use.

There is a need for materials that can be employed in the conventional wash system to minimise damage to, and improve the handle and anti-static properties of the fabrics. At present this effect is obtained in a separate rinse stage after the wash is completed. The active ingredient in a rinse softener is almost invariably a cationic compound. This cationic character, as well as rendering the compound incompatible with the anionic materials generally present in washing compositions because of complex formation and to a lesser extent with nonionic materials as well, also renders the treated fabric water repellent which is disadvantageous for most purposes. Yellowing also frequently occurs on repeated use.

An object of the invention is to provide a material that softens fabrics and is more compatible with the commonly used wash systems than is a cationic and mitigates the water-proofing characteristics of treated fabrics associated with cationics.

The invention provides a zwitterionic surfactant having an acidic hydroxy group with a pKa of 6–10 and a quaternary ammonium group. (By pKa is meant the negative log of the ionisation constant of the acid group of the molecule concerned.) The pH region of interest in a fabric washing operation is from 6 to 11. During the wash the pH's are usually between 8 and 11, while pH's in the rinse solution are 1–2 units lower.

According to the invention the most desirable zwitterionic for this purpose should have a pKa between 7 and 8. Ideally the compound should exist as the zwitterionic form in the wash solution and as the cationic form in the rinse solution. The surfactant characteristics of the new compounds are obtained by inclusion in the molecule of hydrophobic groups. Examples of such hydrophobic groups are an aliphatic group containing from 8 to 20 carbon atoms or an aliphatic group containing an aromatic substituent where the total number of carbon atoms is from 8 to 23. Compounds with a aromatic substituent are particularly effective.

A preferred type of compound within the general class of zwitterionic surfactants is a weak acid betaine. Particularly preferred are hydroxamic betaines of the general formula

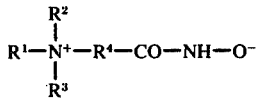

in which $R^1$ is monovalent hydrocabon group having from 1 to 25 carbon atoms, $R^2$ and $R^3$ can be hydroxyalkyl group having from 1 to 4 carbon atoms, or a monovalent hydrocarbon group having from 1 to 25 atoms, or form together a bivalent hydrocarbon group having 4 or 5 carbon atoms, $R^4$ is a bivalent, optionally substituted, methylene, ethylene, propylene or butylene group having not more than 25 carbon atoms, with the proviso that the betaine contains not more than 45 carbon atoms and at least one carbon chain of at least 12 carbon atoms.

For efficient use of the new compounds of the invention the pH of the wash system should be 2–3 pH units higher than the pKa of the acid group and the pH of the rinse as low as practicable. These conditions permit the compounds to exist in the wash system substantially in the zwitterionic forms. Therefore they do not precipitate with the anionic ingredients of the wash system. When the pH is lowered in the rinse, because of dilution, the compounds assume their cationic form resulting in deposition on fabrics. It is important to note that when incorporated in an anionic formulation, the "softening" effect is primarily due to the precipitated complex formed between the cationic form of the weak acid betaine and the relevant anionic. On the other hand in formulations containing a nonionic as the active, the softening is primarily due to the betaine. In most of the cases tested to date the precipitated complex gives better softening than the betaine alone. On rewash the weak acid betaine reverts substantially to the zwitterionic form and is more readily removed than a true cationic. The relationship between pH and structure may be represented as shown below.

When a betaine is dissolved or dispersed in water the following equilibrium holds:

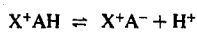

structure at lower pH(P) structure at high pH(Q)

The net charge on species Q is zero and one can roughly describe it as "nonionic", while the net charge on P is positive and this species is cationic. As the pH drops, the equilibrium is shifted in favour of P, effectively producing a cationic release mechanism. Relatively little interaction therefore occurs in the wash (normal pH 8–11) but at the lower rinse pH the increased proportion of species P present gives a good deposition.

This hypothesis has been confirmed by studies of the electrophoretic mobilities of cotton fibres suspended in a solution of the betaines at different pH values. By varying the pH of the system the proportion of cationic betaine present is altered with a corresponding variation in the mobility of the cotton. The proportion of cationic species required to just neutralise the negative sites on the cotton gives the point of null charge for example pH 9.5 Above this pH the cottom appears to be negatively charged and below 9.5 positively charged. The pH of null charge as obtained here is about 2 pH units higher than the pKa of the anionic group of the molecule as obtained by potentiometric titration (ca. 7.5 for a hydroxamic betaine) since only about 1% protonation is required to bring about charge reversal (at pH of 7.5 the betaine is ≈50% in the cationic form). The essential character of the weak acid betaines is exemplified by comparison with other materials. In a solution of cetyl trimethyl ammonium bromide (CTAB) the cotton acquired a positive charge over the complete pH range studied. With the carboxylic betaine $C_{16}H_{33}$ $^+N(CH_3)_2CH_2COO^-$ the null point is much lower and such previously described carboxylic betaines therefore cannot act as effective softeners under practical wash conditions because they will be fully zwitterionic in wash and rinse solutions.

Basically then, the new compounds of the invention are surface active materials containing two groups in the molecule, one which is always positively charged, the other which is uncharged or negatively charged depending on the pH of the environment, and is a weaker acid group than the carboxylic group of previously described betaines.

The preferred compounds are those that do not precipitate with anionic detergents at normal wash pH, i.e. a compound that is primarily in the zwitterionic form at this pH. Compatibility with alkyl benzene sulphonates is most desirable. Improved fabric softening in association with alkylbenzene has been observed, particularly with alkyl benzene sulphonate containing a long chain (i.e. over 15 carbon atoms) alkyl substituent. At the lower pH normally obtained in the rinse it is thought that the cationic form produced by the pH shift reacts with the anionic constituent to form a softening complex that is deposited on the substrate present.

This discovery opens the way to the successful incorporation of an effective fabric softener in a fabric washing composition —something that had not been achieved before the present invention. Additionally, the invention provides a combined washing and fabric-softening composition comprising a compound of the invention and a detergent, preferably an anionic detergent. The invention is also applicable to other detergent compositions, e.g. dishwashing liquids.

It has been observed that mixtures of certain foam-producing surfactants and surfactants of the invention can show variations in foaming performance with pH change. This circumstance is obviously applicable when a detergent formulator wants an anionic-based composition that foams readily when in use (e.g. a dishwashing liquid or shampoo) and whose foam is quenched easily in the rinse. The changes in chemical structure associated with pH change, that is found in the compounds of the present invention, offer a novel and useful way of achieving that end. The decrease in lather is a consequence of a complex formed by the anionic detergent and the cationic form generated in the rinse by the pH change. In general the compound of the invention and the anionic detergent should be present in equimolar amounts to obtain the maximum foam depression in the rinse. In some instances, the foam variation is foam boosting depending on the total carbon chain length of the betaine and the anionic detergent.

A marked increase in rinsability occurs when a compound of the invention is added to a typical high lathering heavy duty detergent for example UK Omo. The amount in gallons of cold 24° H water required to destroy the lather created by a wash with 0.4% Omo is 14½. Up to ≈15% of the stearyl dimethylalkano hydroxamic betaine can be incorporated without markedly affecting the lather in the wash and at that level 2½ gallons of water is required for rinsing as compared to 14½ gallons with Omo alone. At higher levels of the weak acid betaine the foam is destroyed in the wash.

It is also possible to obtain softening effects from the incorporation of the compounds of the invention in nonionic-based formulations. The effect is not so marked as with the anionic/betaine complex. However, any of the weak acid betains according to the Examples, when added at levels of 5-15% to a nonionic formulaion (e.g. US "ALL"), give superior softening to the nonionic alone.

The zwitterionic surfactants of the invention can also be used as conventional rinse conditioners. Obviously by adjusting the pH to suitable levels it is possible to make the compound absorb as a normal long chain cationic to produce marked softening effects. These compounds have some advantage over normal cationics in that they are readily desorbed at higher pH values, i.e. in subsequent washing and hence give less build-up of cationic on the fabric and thereby reducing the undesirable effects of conventional cationics.

The easy dissolution or dispersion of these compounds at normal wash pH (e.g. ther is no hysteresis in the formation or dissolution of the precipitated complex if the pH is adjusted accordingly) gives grounds for the expectation that the zwitterionic surfactant or the anionic complex could give rise to a soil-release action. Dirt which has accumulated between washes will be more readily removed because of the presence of a layer of water-soluble compounds between the dirt and the fabric.

Most conventional cationic and amphoteric surfactants are proven germicides and therefore it is anticipated that the compounds of the invention also possess such properties.

All the following Examples relate to quaternary nitrogen atoms, but the invention is not restricted to the use of these. Other quaternary groups e.g. basic sulphur, will behave in the same way.

A preferred class of compounds according to the invention are the hydroxamic acid betaines.

These compounds can be prepared by reacting hydroxylamine with the appropriate quaternary ester.

Examples of compounds of the invention are:
1. N-stearyl-N,N-dimethyl amino acetohydroxamic betaine

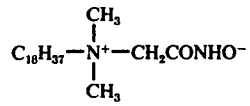

This compound was prepared by conversion of the appropriate quaternary ester to the hydroxamic acid betaine. 4.5 g (0.065M) of hydroxylamine hydrochloride was dissolved in absolute alcohol (100 ml) and to it was added an alcoholic solution of sodium ethoxide until a drop of the solution was pink to phenol phthalein. After cooling the solution sodium chloride was filtered off and the filtrate added to 21 g. (0.05M) of the quaternary ester. After stirring to dissolve the ester the solution was left overnight at room temperature in react. An equivalent amount of sodium ethoxide was added to precipitate more sodium chloride which was filtered off. The product was isolated by the addition of ether and collecting the precipitate.

Analysis for $C_{22}H_{46}N_2O_2$; Found C 69.2, H 12.3, N 6.2; Calc: C 71.3, H 12.4, N 7.6.

Electrophoresis of an 0.01% solution with 0.2% cotton fibres gave a null charge at pH 9.0 when $n = 1$.

Potentiometric titration of 90% ethanol showed an inflexion corresponding to a pKa of 7.5

Tests showed the compound, when incorporated in detergent compositions, had a marked softening effect.

This compound is an example of the class of N-stearyl N,N-dimethylamino alkanohydroxamic acid betaines (SHB). These are preferred compounds, particularly when the alkylene linking group has 1 or 2 carbon atoms.

2. β(N-dodecylbenzyl-N,N-dimethylamino) propiono hydroxamic betaine

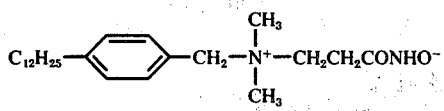

Preparation of methyl β-(N,N-dimethylamino)propionate

Methyl acrylate (90 ml) was poured into a bomb which was cooled with acetone dry ice mixture, and to this was added 184 ml of dimethylamine. The bomb was heated to 40° C at 300 lb pressure and left for two days. Excess of dimethylamine was evaporated and the residue distilled to yield 90 g of methyl β-N,N-dimethylamino propionate boiling at 58°–60°/18 mm.

Analysis for $C_6H_{13}NO_2$; Found: C 53.5, H 10.4, N 10.6; Required; C 55.0, H 10.6, N 10.7.

Preparation of β-dimethylamino propionohydroxamic acid hydrochloride-$(CH_3)_2N \cdot CH_2CH_2CONHOH \cdot HCl$ A solution of 0.1 mole of the ester in 10 ml of water was added with stirring and cooling (0°–5° C), to a solution of 0.1 mole of hydroxylamine hydrochloride in 10 ml of water. The reaction mixture ws stirred for ½ hour at that temperature and left for 24 hours at room temperature. The water was removed under reduced pressure and the residue dissolved in absolute alcohol. The product crystallised out. Yield 14 g. m.p. 88°–90° C, lit. m.p. 91° C.

The aminohydroxamic acid hydrochloride $((CH_3)_2N\ CH_2CH_2COHNOH\ HCl$ 9 g) was dissolved in metanol and neutralised with methanolic potash. The solution was filtered and evaporated to dryness under vacuum. The residue was added to a solution of 18 g of dodecylbenzyl iodide in methyl ethyl ketone and kept for two days at room temperature. The solution was concentrated and ether added to the residue. The product left, after decanting off the ether, was dissolved in alcohol and neutralised with an equivalent amount of alcoholic potash. The solution was evaporated to dryness and the residue dissolved in ether and filtered. The product was isolated by evaporating the ether. Yield 11 g.

Analysis for $C_{24}H_{42}N_2O_2$; Found: C 73.6, H 11.0, N 5.3; Required: C 73.8, H 10.7, N 7.0.

Electrophoresis of 0.01% solutions with 0.2% cotton fibres had a null charge at a pH value of 7.4.

Potentiometric titration by above method gave a pKa of 7.8.

3. β(N-dodecylbenzyl-piperid-N-yl) propionohydroxamic betaine)

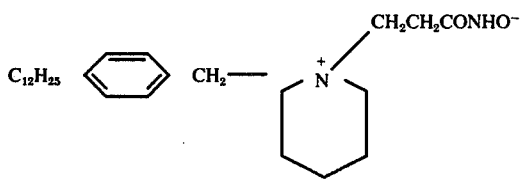

This compound was prepared by a method analogous to that above.

Analysis for $C_{27}H_{46}N_2O_2$; Found: C 76.8, H 11.0 N 5.0; Required: C 75.3, H 10.7, N 6.5.

Electrophoresis of 0.01% solutions with 0.2% cotton fibres has a null charge at a pH value of 8.8.

Potentiometric titration in 90% ethanol gave inflexion corresponding to a pKa of 7.7.

4. N-(dodecyl-hydroxybenzyl)-N,N,N-trimethylammonium iodide

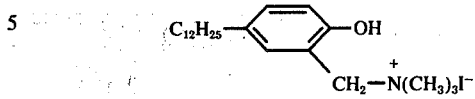

To a solution of 0.2 mol. of dodecylphenol in 100 ml of ethanol was added 0.3 mol of formaldehyde (30% aqueous) and then while cooling and shaking 0.3 mol of dimethylamine (30% ethanolic) was added gradually. The mixture was allowed to stand for 24 hours at room temperature. Two layers formed. The oily layer containing the Mannich base was separated, washed with water and dried. Yield 93%. Equivalent weight 318 (Theoretical 319).

To a solution of 0.2 mol of the above in 100 ml of methanol was added excess metyl iodide and the mixture was refluxed for 3 hours. The product was isolated by removing the excess methyl iodide and methanol.

Analysis for $C_{22}H_{40}INO$; Found: C 57.27, H 8.86, N 3.02; Required; C 57.3, H 8.68, N 3.04.

Electrophoresis as above gave the null charge value of 10.7.

Potentiometric titration as above gave a pKa value of 9.9.

5. N-palmityl-N-phenacyl-N,N-dimethyl-ammonium bromide

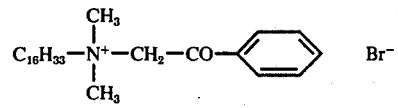

A mixture of hexadecyldimethylamine (0.1 mol) and phenacyl bromide (0.1 mol) in ethanol was refluxed for 5 hours. Ethanol was removed under reduced pressure and the product was crystallised from acetone.

Analysis for $C_{26}H_{46}BrNO$; Found: C 67.3, H 10.0, N 2.7; Required: C 66.66, H 9.83, N 2.99.

Electrophoresis as above gave a null charge at pH 10.5.

6. N-myristyl-N,N-dimethylaminoacetohydroxamic betaine hydrochloride

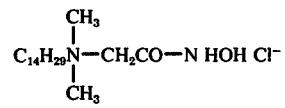

To a solution of hydroxylamine (prepared by dissolving 3 g of hydroxylamine hydrochloride in a minimum quantity of water and neutralised with alcoholic potash at ice temperature) was added a solution of 9 g of the appropriate quaternary ester in alcohol at 0°–5° C. The solution was stirred for ½ hour at that temperature and left for 24 hours at room temperature. The solution was filtered and evaporated to dryness. The residue was dissolved in a small quantity of alcohol and filtered and diluted with ether. The hydroxamic acid betaine hydrochloride came out of solution in a white power form. Yield 7 g.

Analysis for $C_{18}H_{39}N_2O_2Cl$; Found: C 61.77, H 11.36, N 7.57; Required: C 61.7, H 11.14, N 8.0.

The mother liquor on evaporation gave the unreacted ester.

Compositions including the compounds of the invention are:

| | | |
|---|---|---|
| Alkyl benzene sulphonates | $C_{12}$–$C_{18}$ (ABS) | 5–30% |
| Zwitterionic surfactant | | 0.5–15% |
| Sodium tripolyphosphate or other builder | | 20–60% |

Fillers, fluorescers, antiredeposition agents etc. as rest.

It is particularly advantageous to include compatible organic solvents and enzymes and low temperature bleaches to ensure stain removal.

Examples of preferred spray-dried compositions are:

| | | % |
|---|---|---|
| (1) | DOBS-055 (biologically soft sodium dodecylbenzene sulphonate) | 10 |
| | $C_{14}$–$C_{16}$ ABS | 5 |
| | S.H.B. | 8 |
| | TPP | 40 |
| | $Na_2SO_4$ | 15 |
| | Na silicate | 9 |
| | $H_2O$ | 10 |
| | (Fluorescers | |
| | (SCMC | 3 |
| (2) | DOBS–O55 | 15 |
| | S.H.B. | 10 |
| | TPP | 40 |
| | $Na_2SO_4$ | 13 |
| | Na silicate | 9 |
| | $H_2O$ | 10 |
| | (Fluorescers | |
| | (SCMC | 3 |
| (3) | Nonionic-based compositions, e.g. US "All" + 10% SHB | |
| (4) | Nonionic/anionic/soap compositions + 8% SHB | |

What is claimed is:

1. A hydroxamic betaine of the general formula

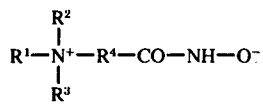

in which $R^1$ is a monovalent hydrocarbon group having from 1 to 25 carbon atoms, $R^2$ and $R^3$ can be a hydroxyalkyl group having from 1 to 4 carbon atoms, or a monovalent hydrocarbon group having from 1 to 25 carbon atoms, $R^4$ is a bivalent, methylene, ethylene, propylene or butylene group, with the proviso that the betaine contains not more than 45 carbon atoms and at least one carbon chain of at least 12 carbon atoms.

2. A hydroxamic betaine according to claim 1 in which $R^1$ is a stearyl group, $R^2$ and $R^3$ are methyl groups, and $R^4$ is a methylene or ethylene group.

3. N-stearyl-N,N-dimethylamino acetohydroxamic betaine.

4. N-myristyl-N,N-dimethylaminoacetohydroxamic betaine hydrochloride.

5. β(N-dodecylbenzyl-N,N-dimethylamino) propionohydroxamic betaine.

* * * * *